United States Patent [19]
DiGuilio et al.

[11] Patent Number: 6,075,168
[45] Date of Patent: Jun. 13, 2000

[54] SELECTIVE PRODUCTION OF DIETHANOLAMINE

[75] Inventors: Ralph M. DiGuilio, Round Rock; Michael W. McKinney, Cedar Park, both of Tex.

[73] Assignee: Huntsman Petrochemical Corporation, Austin, Tex.

[21] Appl. No.: 09/138,134

[22] Filed: Aug. 21, 1998

Related U.S. Application Data

[60] Provisional application No. 60/056,641, Aug. 22, 1997.

[51] Int. Cl.$^7$ .................................................. C07C 209/00
[52] U.S. Cl. ............................................................. 564/487
[58] Field of Search ............................................. 564/487

[56] References Cited

U.S. PATENT DOCUMENTS 5,208,377  5/1993  Overgaard et al. ..................... 564/477

OTHER PUBLICATIONS

Amy R. Ciric and Deyao Gu, "Synthesis of Nonequilibrium Reactive Distillation Processes by MINLP Optimization," *AIChE Journal* 40 (9) pp. 1479–1487, Sep. 1994.

G. G. Podrebarac et al., "More uses for catalytic distillation," *CHEMTEC* May 1997 pp. 37–45.

Amy R. Ciric and Peizhi Miao, "Steady State Multiplicities in an Ethylene Glycol Reactive Distillation Column," Ind. Eng. Chem. Res., (33)1994, pp. 2738–2748.

*Primary Examiner*—Laura L. Stockton
*Attorney, Agent, or Firm*—O'Keefe, Egan & Peterman

[57] ABSTRACT

This invention concerns a process for the production of diethanolamine (DEA) by contacting monoethanolamine (MEA) and ethylene oxide (EO) in a reactive distillation column. The process may achieve high selectivity to DEA.

22 Claims, 3 Drawing Sheets

SELECTIVE PRODUCTION OF DIETHANOLAMINE

This application claims the benefit of U.S. Provisional Application No. 60/056,641 filed Aug. 22, 1997.

BACKGROUND OF INVENTION

This invention relates to a process for the production of diethanolamine from monoethanolamine and ethylene oxide.

The production of ethanolamines is well known. Typically, ethylene oxide (EO) is reacted with aqueous ammonia, which produces a mixture of monomethanolamine (MEA), diethanolamine (DEA), triethanolamine (TEA), and a variety of co-product impurities such as ethylene glycol. It is also well known that the distribution of MEA, DEA, and TEA varies depending on the ammonia/EO ratio. In general, a low ammonia/EO ratio results in a higher TEA level and high ammonia/EO ratio results in a higher level of MEA in the distribution product. DEA production, however, is normally limited to a maximum of about 35% due to the inherent reaction kinetics of the addition reactions. A graph which depicts the varying amounts of ethanolamines depending on ammonia/EO ratios can be found in British Patent 763,932 from 1952.

However, there is a growing need for DEA in certain markets. A process which overcomes the inherent difficulties discussed above, which achieves higher yields of DEA, would therefore be highly desirable.

Also known is reactive distillation to make ethylene glycol from EO and water. Such process are described in Podrebarac et al., "More used for catalytic distillation," CHEMTECH, May, pages 37–45 (1997); Ciric et al., "Steady state multiplicities in an ethylene glycol reactive distillation column," *Ind. Eng. Chem. Res.*, 33(11), pages 2738–2748 (1994); Ciric et al., "Synthesis of nonequilibrium reactive distillation processes by MINLP optimization," *AIChE Journal*, 40(9), pages 1479–1487 (1994). Heretofore, reactive distillation has not be used for the production of alkanolamines.

SUMMARY OF INVENTION

The present invention provides a solution to one or more of the disadvantages and deficiencies described above.

In one broad respect, this invention a process for the production of a dialkanolamine, which comprises: contacting an alkylene oxide and a feed stream comprising monoalkanolamine in a reactive distillation column under reduced pressure such that at least a portion of the monoalkanolamine and alkylene oxide react to form dialkanolamine; allowing the dialkanolamine to fall into a lower portion of the column; heating the dialkanolamine that falls to the lower section of the column to distill any monoalkanolamine that is present along with the dialkanolamine; and collecting a bottoms stream containing dialkanolamine.

The alkylene oxides which may be used in the practice of this invention may vary widely, and typically contain 2 to 20 carbons. Non-limiting examples of such alkylene oxides include ethylene oxide, propylene oxide, butylene oxide, hexylene oxide, and so forth. While a mixture of alkylene oxides may used, it is preferred that a single alkylene oxide is used. Ethylene oxide is the most preferred alkylene oxide used in the practice of this invention. The monoalkanolamine is typically derived from the same alkylene oxide being employed, although a different material may be used if a dialkanolamine is desired having two different alkanol substituents, such as ethanol propanolamine. The preferred products of this invention are derived from ethylene oxide, with the production of diethanolamine being most preferred.

In a second broad respect, this invention is a process for the production of diethanolamine, which comprises: contacting ethylene oxide and a feed stream comprising monoethanolamine in a reactive distillation column under reduced pressure such that at least a portion of the monoethanolamine and ethylene oxide react to form diethanolamine; and collecting a bottoms stream containing diethanolamine.

In another broad respect, this invention is a process for the production of diethanolamine, comprising: contacting ethylene oxide and monoethanolamine a first level to form diethanolamine; allowing the diethanolamine to fall to a second, lower level prior to it reacting with ethylene oxide to form triethanolamine.

This invention has a number of advantages. For example, the invention is highly selectivity to DEA at given MEA/EO ratios. More particularly, the present invention may produce DEA selectivities of greater than 90%. Advantageously, the process may employ feed streams containing a mixture of MEA, DEA, and TEA such as is produced with a conventional aqueous ammonia process. By practice of this invention, MEA may be converted to DEA without existing DEA being further reacted to any appreciable degree.

In addition, it is beneficial that the invention may be implemented using a conventional distillation column. Furthermore, the column simultaneously provides for separation of co-products and reaction of MEA and EO.

The process of this invention may provide improved temperature control of the reaction since the reaction mass is boiling at the local pressure in the tower. The temperature of the reaction may be easily controlled via the tower overhead pressure. Advantageously, the process provides may reduce operating costs from conventional process since reactor coolant is eliminated. Likewise, the reboiler duty may be reduced relative to a conventional tower because the enthalpy of reaction serves to vaporize material within the tower to thereby lower the external heat requirement. The capital costs of implementing the invention may therefore be relatively low. Likewise, the process may be implemented as a retrofit to an existing column.

DETAILED DESCRIPTION OF THE INVENTION

The present invention includes a process to produce a dialkanolamine such as DEA from monoalkanolamine such as MEA and alkylene oxide such as EO in a reactive distillation process. The invention can be practiced over a wide range of conditions. Feed ratios of reactants can vary widely depending on the intended product distribution. While not required, catalysts such as ion exchange resins may be used in the practice of this invention. Advantageously, the process provides a high selectivity to DEA.

Reactive distillation typically takes place within the liquid hold-up on a distillation tray. The volume of the liquid hold-up may influence the extent of reaction on a given tray. It should also be appreciated that in practice, in order to calculate the reaction rates along the column, it is important to know the liquid hold-up. A given hold-up may be accomplished using distillation trays. With trays, the liquid hold-up can be established by changing the weir heights. However, packing may also be used and has the advantage of a lower pressure drop.

In the practice of this invention, monoalkanolamine and alkylene oxide are combined in a column. The reactive distillation column may be comprised of a reaction zone (top section) and a stripping zone (bottom section). The particular type of tower employed is not critical, and many conventional columns may be used. In the reaction zone, MEA and EO for example are contacted and allowed to react. In the stripping section, the MEA is removed from the bottoms stream and returned to the reaction zone. The feed can be either pure MEA or a mixed amine stream. The MEA reacts with EO to form DEA. The reaction between MEA and EO is very fast and proceeds even at room temperature. Thus, the reaction can be carried out over a wide range of temperatures. The upper end of the temperature range is likely set by the amount of by-products which can be tolerated. The temperature is typically in the range from about 100 degrees Fahrenheit to about 400 degrees Fahrenheit, with a temperature of at least 150 degrees Fahrenheit being more typical. Once formed, the heavier DEA falls down the column preferably before it can react to form TEA. The DEA is easily separated to the bottom of the column since it is heavier than MEA and EO, and is thus removed before further reaction with EO to form TEA. Selectivity for DEA may be greater than about 90%, with TEA present in concentrations of about 10% or less. The reactive distillation column may be comprised of a reaction zone (top section) and a stripping zone (bottom section). In the reaction zone, MEA and EO are contacted and allowed to react. In the stripping section, the MEA is removed from the bottoms stream and returned to the reaction zone.

Figure 1:
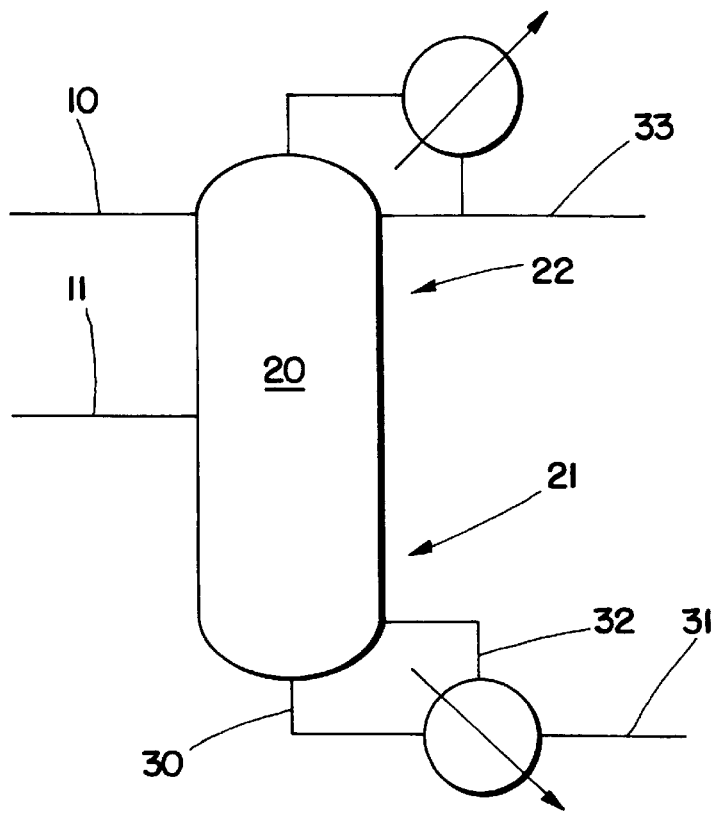
FIGS. 1 and 2 illustrate representative flow sheets for the process of this invention.
Figure 2:
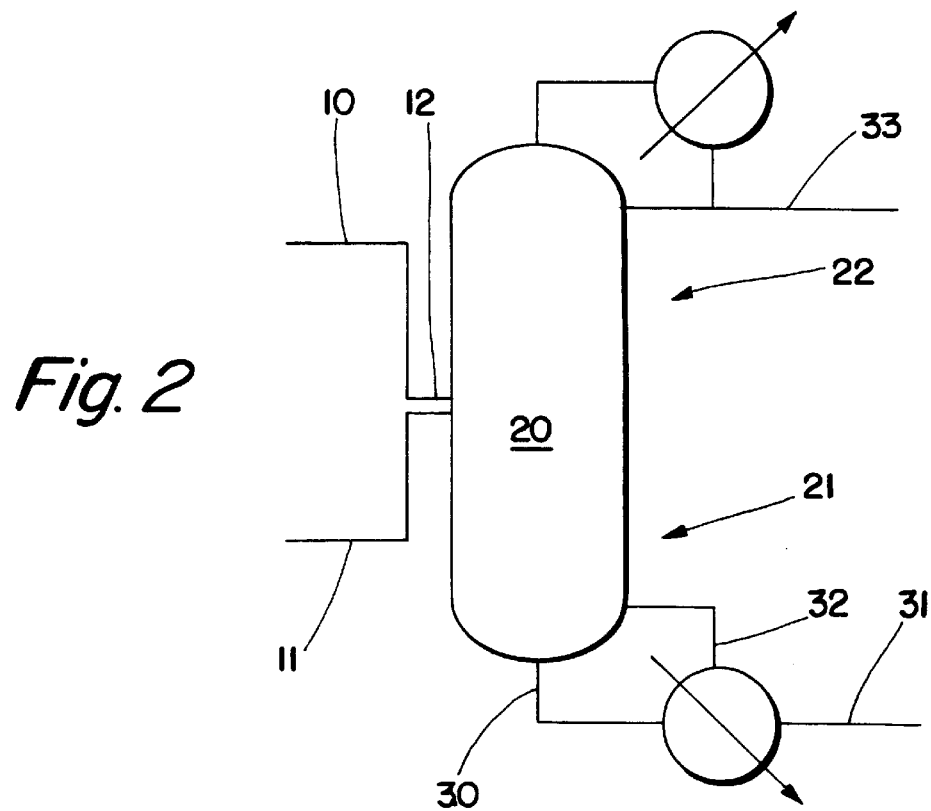

If a pure alkanolamine stream such as a pure MEA stream is available, the stream may be fed anywhere in the column (or "tower") at or above the EO feed point. This may be illustrated in FIG. 1 wherein, for instance, the MEA is fed to column 20 via line 10 with the EO entering column 20 via line 11. However, the preferable place to feed the MEA is near the same point in the column as the EO, as illustrated in FIG. 2 where MEA is fed via line 11 and EO is fed via line 10, with lines 10 and 11 combining to enter the column 20 at point 12. Thus, EO is fed somewhere in the middle of the column 20 and rises through the falling MEA (from the tower reflux). The MEA and EO react in the liquid phase to form DEA. The EO is consumed nearly entirely in the tower so that essentially only MEA is present in the reflux and overhead products of the tower. The heavier DEA reacts with EO to form TEA. In the stripping section 21 of the column 20, any MEA present is vaporized to return to the top of the column 22 (the reaction zone). Such vaporization is facilitated through use of a reboiler at the lower end of the column. The lights that are removed overhead may be removed via conduit 33, and may be recycled to column 20 if desired. The bottoms stream may exit via line 30, with MEA being distilled and returned to column 20 via conduit 32. The DEA-rich stream exits via line 31, optionally for further processing.

In another alternative, an impure stream of alkanolamine may be employed, such as effluent from a typical ethanolamine reactor (after ammonia and water removal) that may include MEA, DEA, and TEA. In this alternative, the MEA stream is fed to about the middle of the column. Referring to FIG. 1, if an impure stream of MEA is used, the MEA stream may be introduced, for example, via line 11 (rather than vice versa as discussed above when using a pure MEA stream) and the EO is fed above the MEA via line 10. When the tower has trays, the EO is fed a few trays above the MEA. The trays between the MEA and EO lines served to separate the MEA from the DEA and TEA. The section of trays above the EO feed is again the reaction zone and the area below the MEA feed is the stripping zone.

Optionally, the process can further separate the DEA from the TEA. Such a process could use a second distillation column in which the DEA would be removed via a side-draw, MEA would be taken overhead, and TEA would be removed as the bottom stream. In a similar process, TEA can be produced from DEA with very little TEA (EO) production.

The overhead may be recycled back to the column to boost the initial MEA:EO ratio fed to the column. The bottoms stream may be further purified using conventional methods such as vacuum distillation technology.

The process of this invention may be operated at under a wide variety of pressures. However, in order to prevent MEA from leaving in the bottoms stream from the column, it is important to operate the column under vacuum. Any conventional column may be used in the practice of this invention. The combination of number of trays or packing height, column diameter, and hold-up on each tray/packing section may be used to determine the pressure that may be employed in the bottom of the column. In general, overhead pressures from about 0.1 to 50 torr (mm Hg) may be used for columns with trays. Such pressures result in sufficiently high temperatures in the MEA/EO reaction zone. In general, the process is operated at a pressure in the range from about 0 pounds per square inch at gauge (psia) to about 1500 psia.

The process of this invention may be automated using standard process control technology. The reactive distillation may be performed with two or more towers that are connected in parallel or in series. The process of this invention may be integrated into an overall scheme to make alkanolamines and may be configured to optimize its placement in a given chemical plant.

Advantageously, this invention may produce dialkanolamine, particularly DEA, in a selectivity of at least about 75%, preferably at least about 80%, and more preferably at least about 85%. The DEA selectivity may be readily controlled by adjusting the reflux ratio of the tower. This invention provides higher selectivities to DEA at a given MEA:EO feed ratio, which is highly advantageous.

In view of the foregoing it is seen that the present invention in one embodiment is a new process for the production of DEA using reactive distillation of MEA and EO. DEA is produced with very high and adjustable selectivities. The process produces DEA almost exclusive of MEA and TEA from essentially stoichiometric amounts of EO and MEA. The invention is useful in the production of DEA to the exclusion of MEA and TEA without the need to use high MEA:EO ratios and providing for removal of MEA from the reaction mass in a single step. The ability to use almost stoichiometric amounts of EO and MEA yet get DEA yields greater than 80–90% (the balance being TEA) is surprising and unexpected.

The following examples are illustrative of this invention and are not intended to be limit the scope of the invention or claims hereto. Unless otherwise denoted all percentages are by weight.

EXAMPLE 1

The process has been simulated using kinetic data for the production of ethanolamines with Aspen Plus™ software. Table 1 shows material and energy balances from a simulation of the reactive distillation process. MEA is fed to the top of a column and EO is fed to the middle. As the EO travels up the column due to its high volatility, it reacts with MEA to form DEA in the liquid supported by the distillation tray. The DEA thus formed travels down the column out of the reaction zone. MEA is also pushed up the column by the reboiler. In this way, reaction zone with a very high MEA:EO ratio is created allowing for very selective production of DEA.

TABLE 1

| Stream ID | Units | Bottoms | EO-Feed | L-Overhead | MEA-Feed |
|---|---|---|---|---|---|
| Temp. | Fahrenheit | 388.9 | 100.0 | 205.3 | 250.0 |
| Pressure | PSI | 1.55 | 60.0 | 0.97 | 60.0 |
| Vapor Fraction | | 0 | 0 | 0 | 0 |
| Mole flow | LBMOL/HR | 46.447 | 49.94 | 14.144 | 60.573 |
| Mass flow | CUFT/HR | 83.178 | 41.537 | 14.622 | 63.425 |
| Enthalpy | MMBTU/HR | −9.210 | −1.644 | −1.587 | −6.574 |
| Water | | trace | | | |
| EO | | trace | 2200 | 0.815 | |
| NH3 | | trace | | | |
| MEA | | 23.109 | | 848.130 | 3700 |
| DEA | | 4458.859 | | 24.841 | |
| TEA | | 536.860 | | 0.581 | |
| DGA | | 5.883 | | 0.032 | |
| EG | | trace | | trace | |
| TEA-EO | | 0.89 | | <0.001 | |
| Mass Fraction | | | | | |
| WATER | | trace | | | |
| EO | | trace | 1.0 | 932 ppm | |
| NH3 | | trace | | | |
| MEA | | 0.005 | | 0.97 | 1.0 |
| DEA | | 0.887 | | 0.028 | |
| TEA | | 0.107 | | 664 ppm | |
| DGA | | 0.001 | | 36 ppm | |
| EG | | trace | | trace | |
| TEA-EO | | 177 ppm | | 310 ppb | |
| Mole Flow | | | | | |
| WATER | | trace | | | |
| EO | | trace | 49.94 | 0.018 | |
| NH3 | | trace | | | |
| MEA | | 0.378 | | 13.885 | 60.573 |
| DEA | | 42.410 | | 0.236 | |
| TEA | | 3.598 | | 0.004 | |
| DGA | | 0.056 | | <0.001 | |
| EG | | trace | | trace | |
| TEA-EO | | 0.005 | | trace | |

Below the EO feed, an MEA stripping section removes the unreacted MEA from the bottoms product which consists of DEA and a little TEA. Either packing or trays can be used in the tower design as a catalyst is not needed.

In this example, 2200 pounds per hour ("lbs/hr") of EO and 3200 lbs/hr MEA are fed to the middle and top of a distillation column. The overhead product is 874 lbs/hr MEA plus trace (<1 lb/hr) unreacted EO. The bottoms product is 4460 lbs/hr DEA and 566 lbs/hr TEA. The MEA is recycled to either the column or a front-end reactor. The temperature of the reaction is controlled by the pressure of the column. The net yield of DEA is 88.7 weight percent from essentially stoichiometric amounts of EO and MEA.

In a slight variation, accommodation can be made for any residual ammonia or water present from the reactor effluent by the use of a side draw. The overhead product (a very small stream) consists of ammonia, water, residual EO and some MEA. The bulk of unreacted MEA is taken as a side-draw. This eliminates the need for a de-watering tower. (Even in processes using anhydrous ammonia, some water is present in the feed ammonia and some is created in the reboilers due to decomposition of the ethanolamines, still other water results from condenser/reboiler leaks.)

By comparison, the reaction of EO and MEA will result in about equal amounts of DEA and TEA since the reaction rate between MEA and EO is slightly slower than that of DEA and EO. Rapid removal of DEA from the reaction zone allows for the high selectivity to DEA.

EXAMPLE 2

Figure 3:
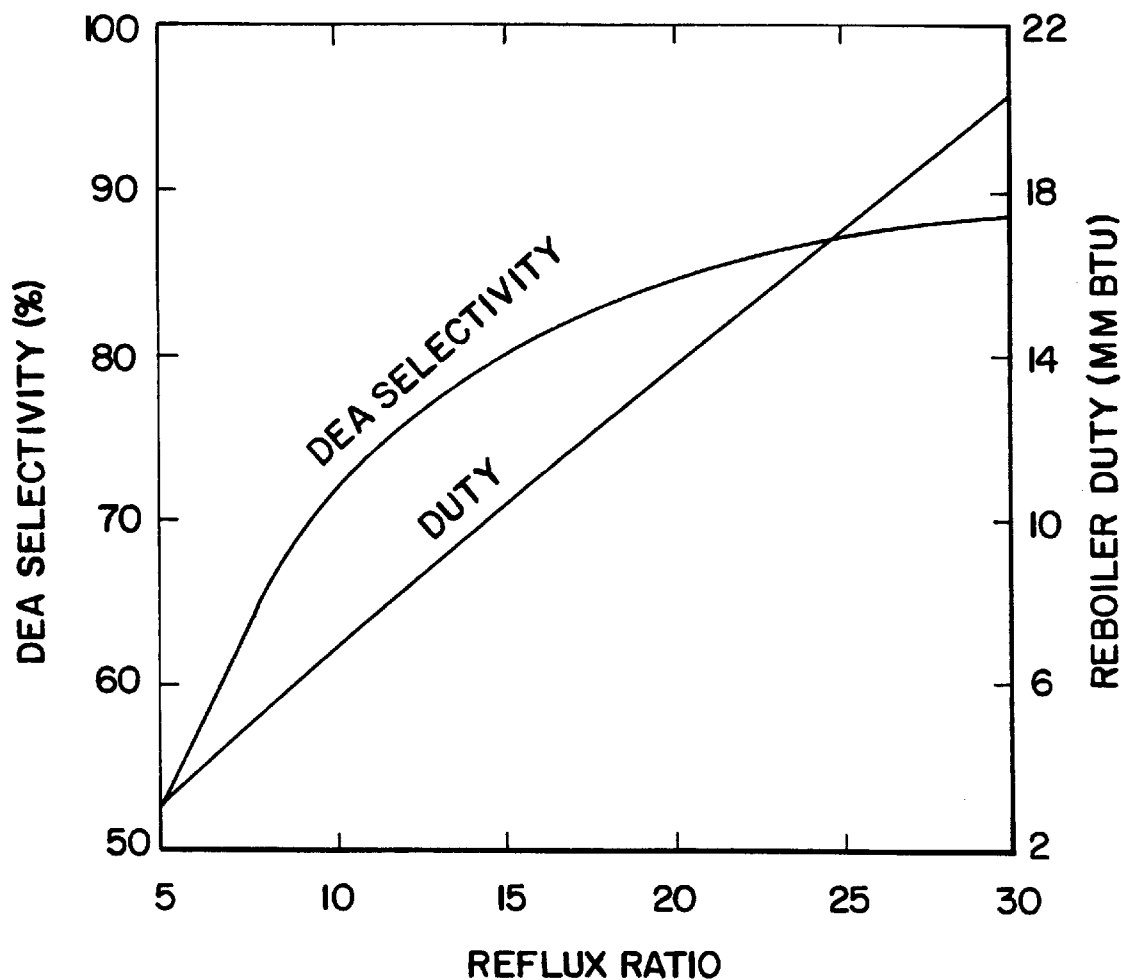
FIG. 3 illustrates the effect of tower reflux ratio on DEA selectivity and reboiler duty from a mixed ethanolamine feed stream.

Employing the configuration of FIG. 2, material and energy balances were calculated for a 20 foot diameter column with 15 theoretical trays. The tower feed was 9000 and 5500 pounds/hour of MEA and EO, respectively. The EO and MEA are fed to tray 11. The (molar) reflux ratio used is 20. The hold-up per tray is set at 80 cubic feet ($ft^3$) for trays 2 through 11. This corresponds to an approximate weir height of 3 inches. For pressure drop calculations, trays 2–11 are taken as sieve trays, trays 12–14 are taken to be Sulzer BX™ wire mesh tower packing. In the feed to the tower, the molar ratio of MEA:EO is 1.18 yet the selectivity to DEA is 85%. To achieve similar selectivity in a plug flow reactor, an MEA:EO mole ratio of about 3.6 is required (as per the calculations of Lowe's British Patent Number 763,932 (1956)). One of the important features of this invention is that the selectivity to DEA is adjustable via the reflux ratio. In this regard, FIG. 3 shows the effect of reflux ratio on selectivity. The results of the calculations using the Aspen Plus™ process simulator is shown in Table 2.

TABLE 2

| Stream ID | Units | Bottoms | EO-Feed | L-Overhead | MEA-Feed |
|---|---|---|---|---|---|
| Temp. | Fahrenheit | 390.0 | 100.0 | 140.0 | 250.0 |
| Pressure | PSI | 1.42 | 60.0 | 0.58 | 60.0 |
| Vapor Fraction | | 0 | 0 | 0 | 0 |
| Mole flow | LBMOL/HR | 112.168 | 124.849 | 35.218 | 147.339 |
| Volume flow | CUFT/HR | 203.854 | 103.843 | 35.053 | 154.277 |
| Mass flow | LB/HR | 12343.159 | 5500.0 | 2156.841 | 9000.0 |
| Enthalpy | MMBTU/HR | −22.567 | −4.110 | −4.010 | −15.990 |
| Mass flow | | | | | |
| Water | | | | | |
| EO | | trace | 5500.0 | 2.094 | |
| NH3 | | trace | | trace | |
| MEA | | 14.031 | | 2139.516 | 9000.0 |
| DEA | | 10420.319 | | 15.127 | |
| TEA | | 1889.065 | | 0.084 | |
| DGA | | 14.349 | | 0.020 | |
| EG | | | | | |
| TEA-EO | | 5.393 | | <0.001 | |

EXAMPLE 3

Figure 4:
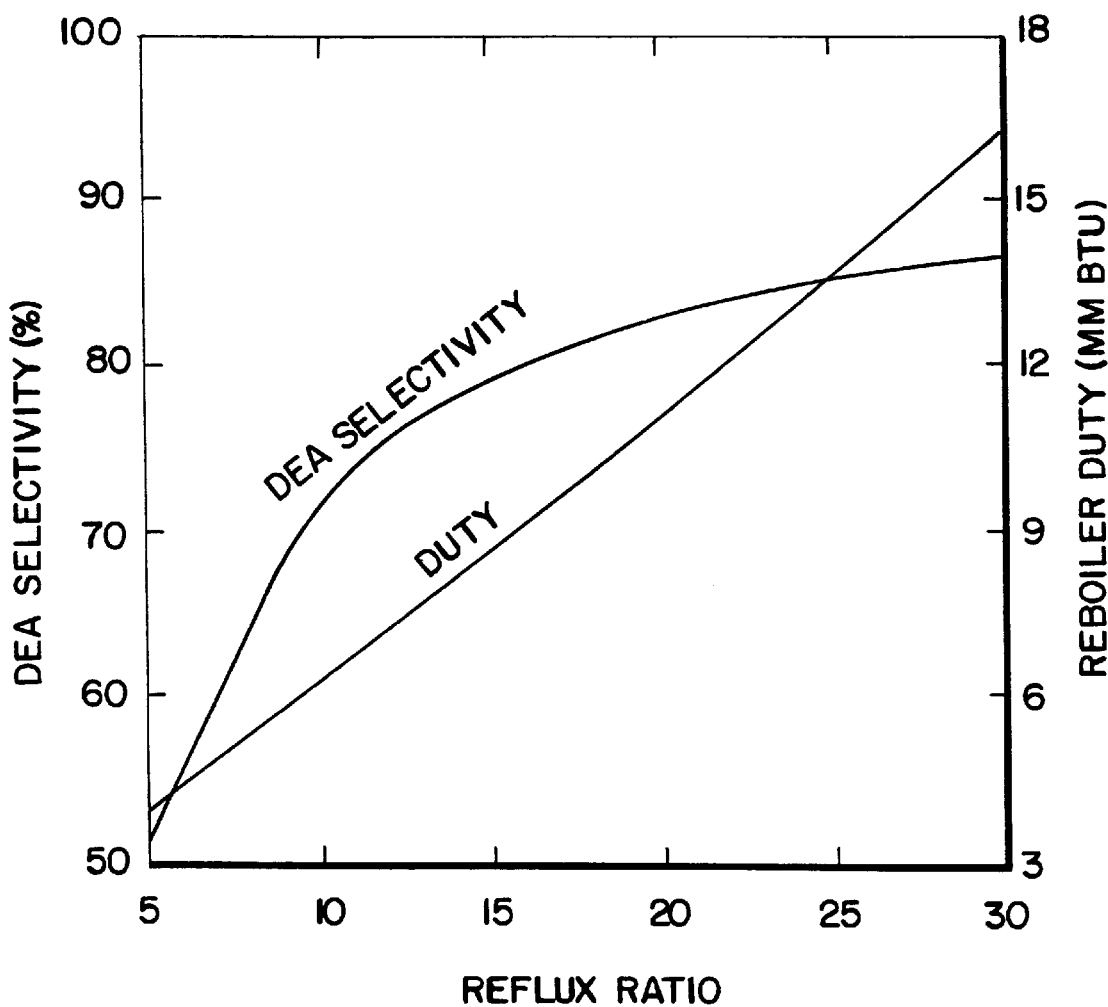
FIG. 4 illustrates the effect of tower reflux ratio on DEA selectivity and reboiler duty for a substantially pure MEA feed stream.

The material and energy balances for a mixed amine feed were calculated using the Aspen Plus™ process simulator. The feed contains 6200, 3100, 700, and 3700 lbs/hour of MEA, DEA, TEA, and EO, respectively. The feed is meant to correspond to that from a typical ethanolamines reactor operating with about a 5:1 NH3:EO ratio combined with the overhead from the tower which is recycled to the feed. Again a 20 foot diameter, 15 theoretical tray tower is used. The mixed amine is fed to tray 12 and the EO to tray 9. The hold-ups for trays 2–12 are 80 cubic feet. Trays 2–12 are taken as sieve trays and trays 13–14 are taken as Sulzer BX™ wire mesh packing for pressure drop calculations. FIG. 4 shows the effect of reflux ratio on DEA selectivity and reboiler duty. The results of the calculations are shown in Table 3.

TABLE 3

| Stream ID | Units | Bottoms | EO-Feed | L-Overhead | MEA-Feed |
|---|---|---|---|---|---|
| Temp. | Fahrenheit | 390.0 | 100.0 | 140.0 | 250.0 |
| Pressure | PSI | 1.53 | 60.0 | 0.68 | 60.0 |
| Vapor Fraction | | 0 | 0 | 0 | 0 |
| Mole flow | LBMOL/HR | 109.892 | 83.989 | 25.804 | 135.677 |
| Volume flow | CUFT/HR | 200.125 | 69.858 | 25.668 | 165.215 |
| Mass flow | LB/HR | 12120.706 | 3700.0 | 159.293 | 10000.0 |
| Enthalpy | MMBTU/HR | −22.135 | −2.765 | −2.936 | −18.328 |
| Mass flow | | | | | |
| Water | | trace | | trace | |
| EO | | trace | 3700 | 0.816 | |
| NH3 | | trace | | trace | |
| MEA | | 56.971 | | 1570.348 | 6200 |
| DEA | | 9997.207 | | 8.086 | 3100 |
| TEA | | 2052.547 | | 0.033 | 700 |
| DGA | | 9.583 | | 0.011 | |
| EG | | | | | |
| TEA-EO | | 4.399 | | trace | |

Further modifications and alternative embodiments of this invention will be apparent to those skilled in the art in view of this description. Accordingly, this description is to be construed as illustrative only and is for the purpose of teaching those skilled in the art the manner of carrying out the invention. Equivalent elements may be substituted for those illustrated and described herein, and certain features of the invention may be utilized independently of the use of other features, all as would be apparent to one skilled in the art after having the benefit of this description of the invention.

What is claimed is:

1. A process for the production of a dialkanolamine, which comprises: contacting an alkylene oxide and a feed stream comprising monoalkanolamine in a reaction section of a distillation column under reduced pressure such that at least a portion of the monoalkanolamine and alkylene oxide react to form dialkanolamine; allowing the dialkanolamine to fall into a lower portion of the column; heating the dialkanolamine that falls to the lower section of the column to distill any monoalkanolamine that is present into the reaction zone; and collecting a bottoms stream containing dialkanolamine.

2. A process for the production of diethanolamine, which comprises: contacting ethylene oxide and a feed stream comprising monoethanolamine in a reactive distillation column such that at least a portion of the monoethanolamine and ethylene oxide react to form diethanolamine; and collecting a bottoms stream containing diethanolamine.

3. The process of claim 2 wherein the reactive distillation column is maintained at a pressure in the range from about 0 to about 1500 pounds per square inch.

4. The process of claim 2 wherein a pressure of from about 0.1 mm Hg to about 50 mm Hg for overhead pressure.

5. The process of claim 2 wherein the contacting occurs in the upper half of the column.

6. The process of claim 2 further comprising heating the bottoms stream to vaporize any monoethanolamine in the bottoms stream back into the column.

7. The process of claim 2 further comprising separating diethanolamine from the bottoms stream.

8. The process of claim 2 wherein the temperature during contacting is maintained in the range from about 100 degrees Fahrenheit to about 400 degrees Fahrenheit.

9. The process of claim 2 wherein the contacting is conducted in the absence of a catalyst.

10. The process of claim 2 wherein the column is a packed column or is a column with one or more trays.

11. The process of claim 2 wherein monomethanolamine is collected overhead and recycled to the reactive distillation column.

12. The process of claim 2 operated to provide a selectivity to diethanolamine of at least about 85%.

13. The process of claim 2 wherein the monoethanolamine feed stream also contains monoethanolamine, triethanolamine, or both.

14. The process of claim 2 wherein the ethylene oxide is introduced into the column above the monoethanolamine.

15. The process of claim 2 wherein the ethylene oxide is introduced into the column below the monoethanolamine.

16. The process of claim 2 wherein the ethylene oxide and monoethanolamine are introduced into the column at about the same point.

17. The process of claim 2 wherein unreacted monoethanolamine that falls to the bottom of the column is heated to distill it upwards for further contact with ethylene oxide.

18. The process of claim 2 wherein overhead collected off the top of the column is recycled to the column.

19. A process for the production of diethanolamine, comprising:

contacting ethylene oxide and monoethanolamine in a first level to form diethanolamine;

allowing the diethanolamine to fall to a second, lower level prior to the diethanolamine reacting with ethylene oxide in the first level to form triethanolamine.

20. The process of claim 19 in which the contacting occurs in a reactive distillation column.

21. The process of claim 20 wherein a reboiler boils any unreacted monoethanolamine that falls to the second, lower level so that the monoethanolamine rises to the first level for contact with ethylene oxide.

22. The process of claim 19 wherein the contacting occurs at a temperature in the range from about 100 degrees Fahrenheit to about 400 degrees Fahrenheit.

\* \* \* \* \*